US 6,579,442 B2

(12) United States Patent
Eldin

(10) Patent No.: US 6,579,442 B2
(45) Date of Patent: Jun. 17, 2003

(54) METHODS AND COMPOSITIONS FOR INHIBITING POLYMERIZATION OF VINYL MONOMERS

(75) Inventor: Sherif Eldin, Houston, TX (US)

(73) Assignee: GE Betz, Inc., Trevose, PA (US)

( * ) Notice: Subject to any disclaimer, the term of this patent is extended or adjusted under 35 U.S.C. 154(b) by 22 days.

(21) Appl. No.: 09/862,405

(22) Filed: May 22, 2001

(65) Prior Publication Data

US 2003/0010676 A1 Jan. 16, 2003

(51) Int. Cl.[7] .............................. C07C 7/20; C10G 7/10; C10G 9/16; C07B 63/04
(52) U.S. Cl. ................... 208/48 AA; 208/92; 208/184; 208/255; 208/289; 208/348; 585/4; 585/5; 203/8; 203/9
(58) Field of Search ........................ 208/48 AA, 48 R, 208/92, 184, 255, 289, 348; 203/8, 9; 585/4, 5

(56) References Cited

U.S. PATENT DOCUMENTS

| 3,148,225 | A |   | 9/1964 | Albert ...................... 260/669 |
|---|---|---|---|---|
| 3,342,723 | A |   | 9/1967 | Godar ......................... 208/48 |
| 3,488,338 | A |   | 1/1970 | Bailey et al. ............... 206/92.3 |
| 3,733,326 | A |   | 5/1973 | Murayama et al. ......... 260/290 |
| 3,747,988 | A |   | 7/1973 | Bailey ........................... 203/8 |
| 4,670,131 | A |   | 6/1987 | Ferrell ................... 208/48 AA |
| 4,720,566 | A |   | 1/1988 | Martin ....................... 558/306 |
| 5,221,498 | A | * | 6/1993 | Reid et al. .................. 252/403 |
| 5,254,760 | A |   | 10/1993 | Winter et al. ................... 585/5 |
| 5,258,138 | A |   | 11/1993 | Gatechair et al. ........... 252/403 |
| 5,510,547 | A |   | 4/1996 | Arhancet et al. ............... 585/5 |
| 5,711,767 | A |   | 1/1998 | Gande et al. ................. 44/423 |
| 5,728,872 | A |   | 3/1998 | Riemenschneider ........ 562/598 |
| 5,888,356 | A |   | 3/1999 | Keil et al. ...................... 203/8 |
| 6,200,461 | B1 |   | 3/2001 | Eldin .................... 208/48 AA |
| 6,379,588 | B1 | * | 4/2002 | Sutoris et al. .............. 252/405 |

FOREIGN PATENT DOCUMENTS

| EP | 0 467 849 B1 | 4/1995 | .......... C07C/69/54 |
|---|---|---|---|
| WO | 98/02400 | 1/1998 | .......... C07B/63/04 |

* cited by examiner

Primary Examiner—Bekir L. Yildirim
(74) Attorney, Agent, or Firm—Steven D. Boyd

(57) ABSTRACT

Methods and compositions for inhibiting the polymerization of vinyl monomers are disclosed. Combinations of nitroxyl compounds and aliphatic amines are effective at inhibiting the polymerization of vinyl monomers under both processing and storage conditions.

19 Claims, 3 Drawing Sheets

METHODS AND COMPOSITIONS FOR INHIBITING POLYMERIZATION OF VINYL MONOMERS

FIELD OF THE INVENTION

The present invention provides for methods and compositions for inhibiting the polymerization of vinyl monomers, such as olefins and diolefins.

BACKGROUND OF THE INVENTION

Common industrial methods for producing vinyl monomers include a variety of purification processes such as distillation to remove impurities. Purification operations are often carried out at elevated temperatures and this can increase the rate of undesired polymerization. Polymerization, such as thermal polymerization, during the monomer purification process, results not only in loss of desired monomer end-product, but also in production efficiency caused by polymer formation and deposition on process equipment. Undesirable polymerization causes monomer loss, and may cause operational problems such as increase in fluid viscosity, temperature, restricted flow in pipelines, and block filters. In heat requiring operations, such deposition adversely affects heat transfer efficiency.

Typically the monomers are stabilized with the addition of substances which will act as inhibitors or retarders of polymerization.

Certain vinyl monomers such as the diolefins butadiene and isoprene will polymerize when left in storage tanks and during transportation at temperatures as low as room temperature. This polymerization is initiated by reaction of the diolefin monomer with oxygen present in the monomer containing system. This reaction will form peroxides and free radical species which will perpetuate the reaction with the diolefin monomer.

Various approaches have been attempted with regard to this problem of polymerization. U.S. Pat. No. 3,148,225 teaches that N,N-dialkylhydroxylamines will inhibit the polymerization of popcorn polymer formation in olefin monomer recovery systems. In comparative studies, p-aminophenol was less effective than the hydroxylamines at inhibiting popcorn polymer formation. U.S. Pat. No. 6,200,461 teachs the use of combinations of aminophenols with dialkylhydroxylamines or phenylenediamines. U.S. Pat. No. 3,342,723 tests p- and o-aminophenols for inhibiting fouling of hydrocarbon liquids. These compounds proved effective at inhibiting the formation and adhesion of coke-like deposits during refinery operations.

U.S. Pat. No. 5,510,547 teaches that a combination of a phenylenediamine compound and a hydroxylamine compound is effective at inhibiting the polymerization of vinyl aromatic monomers during processing conditions. U.S. Pat. No. 4,720,566 teaches that a combination of a hydroxylamine and a phenylenediamine compound is effective at inhibiting the polymerization of acrylonitrile during its production.

The use of 2,2,6,6-teteramethylpiperidine-N-oxyl (nitroxyl radical) based stable free radicals for controlling free radical polymerization of reactive monomers is well established in literature. U.S. Pat. No. 3,747,988 teaches its use for controlling acrylonitrile polymerization, U.S. Pat. No. 3,733,326 teaches its use for stabilizing vinyl monomers, U.S. Pat. No. 3,488,338 teaches its use for short-stopping the polymerization of chloroprene, U.S. Pat. No. 4,670,131 claims the use of nitroxyl radicals in the range of 20 ppb to 700 ppm for controlling fouling of vinyl monomers.

TEMPO-based nitroxyl radicals are relatively expensive. Synergistic combinations of nitroxyl radicals with other compounds have benefits (economic and technical) and there are a number of patents that teach these types of combinations. Examples are; U.S. Pat. No. 5,711,767 for the use of nitroxyl radical molecules with phenylenediamines to prevent gum formation in gasoline, U.S. Pat. No. 5,888,356 for the use of nitroxyl radicals with nitrosophenols for stabilizing vinyl monomers, U.S. Pat. No. 5,728,872 for the use of nitroxyl radicals with dihetero-substituted benzene for stabilizing acrylic acid, and U.S. Pat. No. 5,254,760 for the use of nitroxyl radicals with aromatic nitro compounds for stabilizing vinyl aromatic monomers. U.S. Ser. No. 09/862,406 teaches the use of nitroxyl compounds in combination with aminophenols to inhibit polymerization of vinyl monomers.

DETAILED DESCRIPTION OF THE INVENTION

Figure 1:
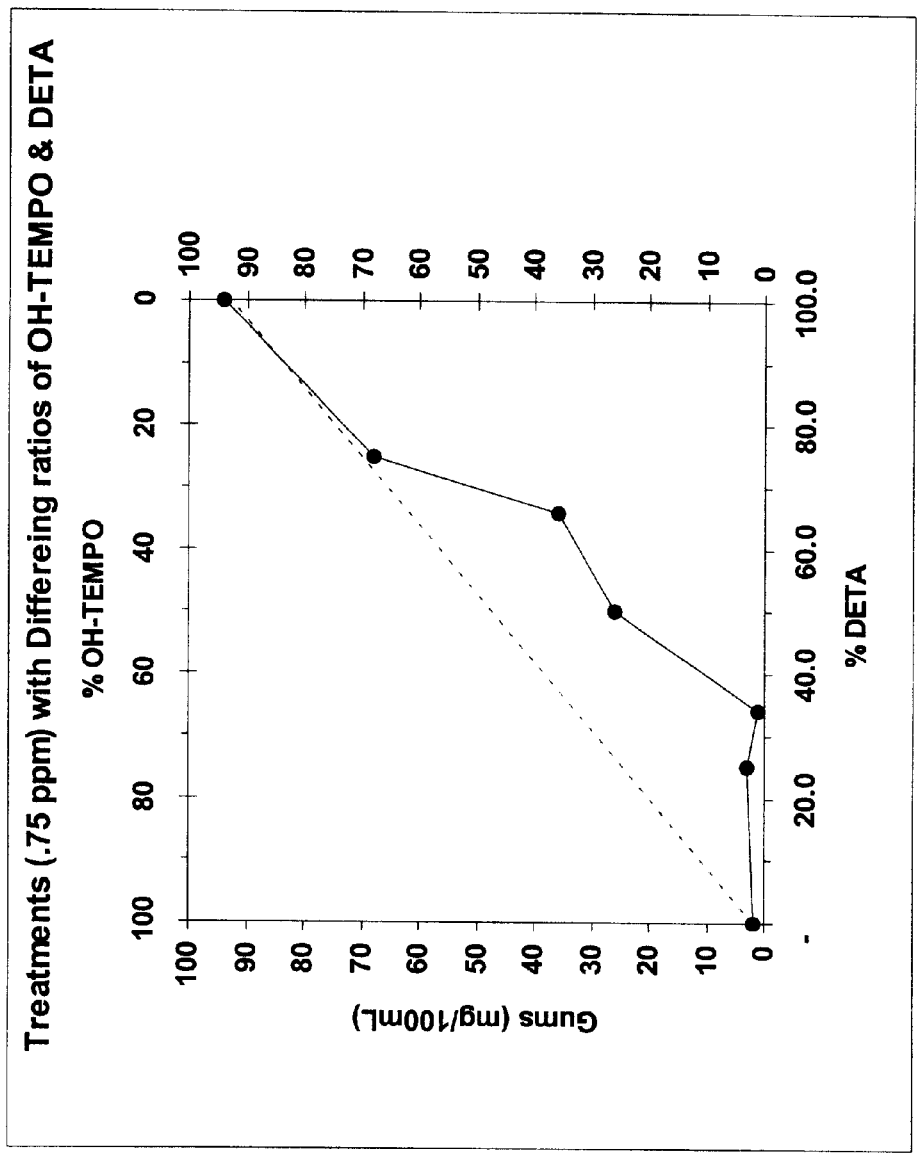
FIG. 1 depicts gum formation versus composition component ratio for components tested under Example 1 with the results reported in Table I below.

The present invention provides for methods and compositions for inhibiting the polymerization of vinyl monomers comprising adding an effective inhibiting amount of an inhibitor composition comprising (A) an aliphatic amine and (B) a nitroxyl radical compound.

The aliphatic amine compounds useful in the present invention include, without limitation, ethylenediamine (EDA), diethylenetriamine (DETA), butane-1,4-diamine, ethylamine, propylamine, butylamine, pentylamine, hexylamine, and cyclohexylamines.

Exemplary nitroxyl radical compounds include, but are not limited to derivatives of dialkyl nitroxyl radicals and 1-oxyl-2,2,6,6-tetraalkylpiperidine compounds such as 1-oxyl-2,2,6,6-tetramethylpiperidine, 1-oxyl-2,2,6,6-tetramethylpiperidin-4-ol (OH-TEMPO), 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl)terephthallate, bis(1-oxyl-2,2,6,6-tetramethylpiperidin-4-yl)hexahydroterephthalate, N,N'-bis(1-oxyl-2,2,6,6-tetramethylpiperidin-4-yl)adipamide, N-1-oxyl-2,2,6,6-tetramethylpiperidin-4-yl-dodecylsuccinimide, 1-oxyl-4-methoxy-2,2,6,6-tetramethylpiperidine, 1-oxyl-4-amino-2,2,6,6-tetramethylpiperidine and 1-oxyl-4-acetamino-2,2,6,6-tetramethylpiperidine.

The monomers are characterized as polymerizable vinyl monomers and include olefins and diolefins. The olefins contain about 2 to about 20 carbon atoms, preferably 2 to 8 carbon atoms and the diolefins are conjugated and contain about 4 to about 20 carbon atoms with 4 to 6 carbon atoms preferred. Examples of these compounds include ethylene dichloride, vinyledene chloride, ethylene glycol, aromatics from ethylene plants and pyrolysis gasoline, butadiene, isoprene and cyclopentadiene, vinylacetate, acrylonitile, methacrylic acid, and methylmethacrylate.

The inhibitor compositions of the present invention are effective at inhibiting the polymerization of vinyl monomers during both storage and processing conditions. Storage conditions also include transportation of the monomers. These conditions will usually have oxygen present and can be at elevated temperatures of up to 100° C. The processing conditions are usually distillation and purification processes and are run at elevated temperatures of 50° and 150° C. where oxygen can be present or absent.

For purposes of the present invention, the term "effective amount for the purpose" is that amount of inhibitor compositions necessary to reach the desired level of inhibition of the polymerization of the vinyl monomers. This amount will vary according to the conditions under which the monomers are subjected during the storage and/or handling thereof, and one skilled in the art may readily determine the effective total amount of inhibitor composition needed to reach the desired level of inhibition for the application of interest. During processing, for example, high temperatures and higher monomer contamination will require larger amounts of the inhibitor compositions.

Preferably, the total amount of the inhibitor compositions added to the vinyl monomer will range from about 1 part to about 10,000 parts per million parts of monomer. More preferably, the inhibitor compositions are added at a range of about 1 part to about 100 parts per million parts monomer.

The weight ratio of aliphatic amine compound to nitroxyl radical compound in the inhibitor composition can generally vary from about 1:9 to about 9:1.

Accordingly, it is possible to produce a more effective vinyl monomer polymerization inhibition treatment than is obtainable by the use of one ingredient alone when measured at comparable treatment levels. This enhanced activity will allow for the concentration of each of these ingredients to be lowered and the total quantity of polymerization inhibitor particularly at higher processing temperatures may be reduced.

The inhibitor compositions of the present invention may be added to the vinyl monomers as either a dispersion or as a solution using a suitable liquid carrier or solvent. Any solvent that is compatible with the individual ingredients and with the monomer may be employed. The compositions may be introduced by any conventional method at any point in the processing system.

The inhibitor compositions may be added to the vinyl monomers by any conventional method, either as individual components or as a combination of components. It is preferred that the ingredients be added to the monomer as a single treatment.

This invention will now be further described with reference to a number of specific examples which are to be regarded solely as illustrative and not as restricting the scope of the invention.

EXAMPLE 1

20% uninhibited isoprene in heptane was dosed with different treatments and placed in a pressure vessel. This mixture was then purged once with nitrogen before placing it under 100 psi nitrogen. The pressure vessel was then placed in a 100° C. water bath for 4 hours allowing polymerization of the diolefin. The mixture was then allowed to cool at room temperature. The sample was evaporated and the remaining gums/polymer weight was obtained.

The results of this testing for varying ratios of the combination of DETA (diethylenetriamine) and OH-TEMPO are presented in Table I and FIG. 1.

TABLE I

| No. | % OH-TEMPO | % DETA | Total (ppm) | Gums (mg/100 ml) |
|---|---|---|---|---|
| 1 | 100 | 0.0 | 0.75 | 2 |
| 2 | 75 | 25 | 0.75 | 3 |
| 3 | 67 | 34 | 0.75 | 1 |
| 4 | 50 | 50 | 0.75 | 26 |
| 5 | 34 | 66 | 0.75 | 36 |
| 6 | 25 | 75 | 0.75 | 68 |
| 7 | 0.0 | 100 | 0.75 | 94 |

These results demonstrate that the combination of DETA and OH-TEMPO is synergistic and unexpectedly more effective than would have been predicted by a linear combination of the particular individual components.

EXAMPLE 2

Figure 2:
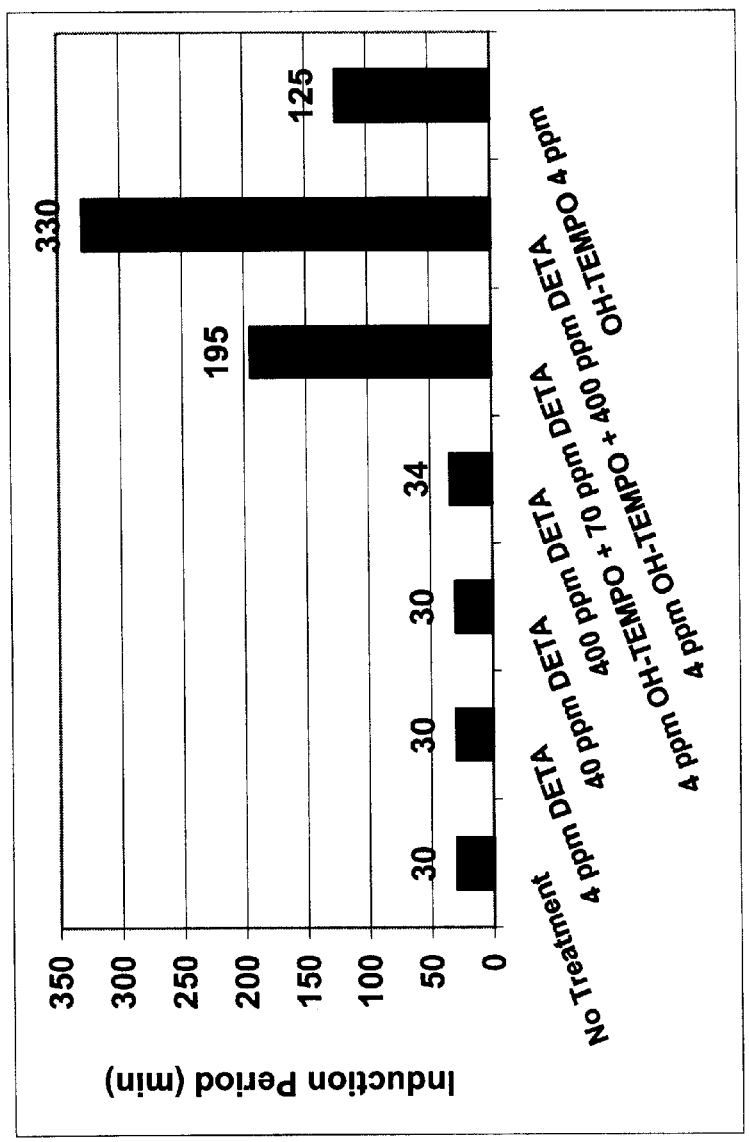
FIG. 2 is a graph of induction period versus composition component ratio for several treatments as tested in Example 2 with results reported in Table II below.
Figure 3:
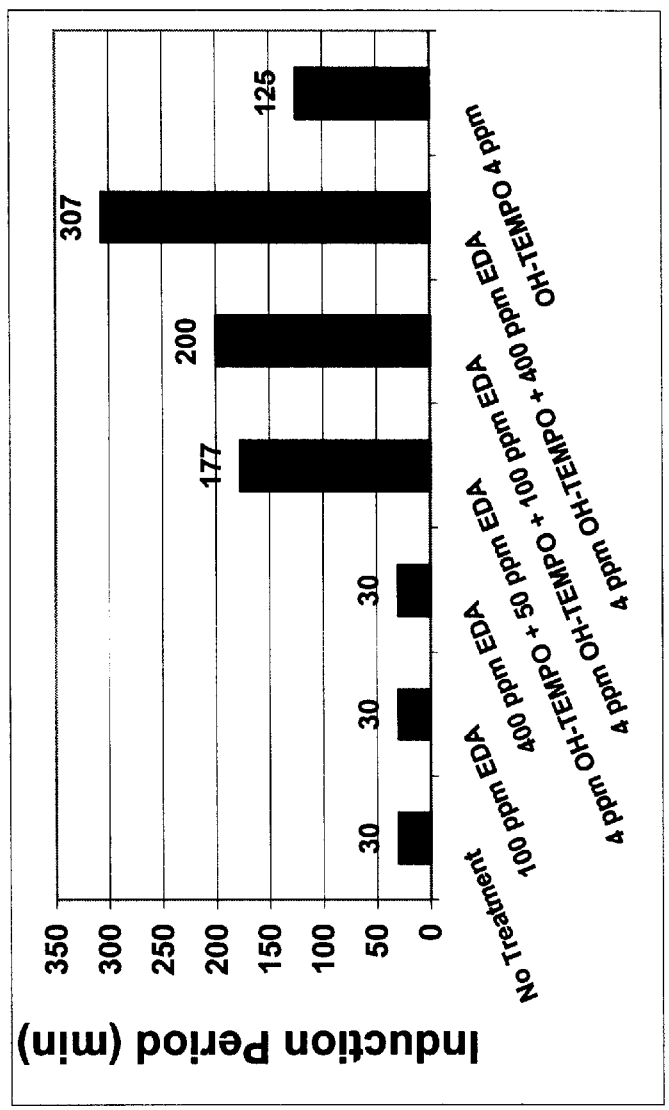
FIG. 3 depicts induction period results for compositions tested and reported in Table III below.

The effectiveness of different treatments in controlling monomer polymerization in the presence of oxygen was tested using the oxidation stability test, also known as the induction period test (ASTM D 525). 20% uninhibited isoprene in heptane was dosed with different treatments and placed in a pressure vessel. This mixture was then placed under 100 psi oxygen. The pressure vessel was then placed in a 100° C. water bath for 4 hours allowing polymerization of the diolefin. The oxygen pressure in the vessel was monitored and the induction period to oxygen pressure drop was recorded. The results are depicted in Tables 2, 3 and 4 and FIGS. 2 and 3.

TABLE II

| No. | OH-TEMPO (ppm) | DETA (ppm) | Total (ppm) | Induction (min.) |
|---|---|---|---|---|
| 1 | 0.0 | 0.00 | 0.0 | 30 |
| 2 | 0.0 | 4 | 4 | 30 |
| 3 | 0.0 | 40 | 4 | 30 |
| 4 | 0.0 | 400 | 400 | 34 |
| 5 | 4 | 70 | 74 | 195 |
| 6 | 4 | 400 | 404 | 330 |
| 7 | 4 | 0.0 | 4 | 125 |

Table III presents the results of testing a combination of OH-TEMPO with EDA (ethylenediamine) under the same conditions and at comparable concentrations and ratios.

TABLE III

| No. | OH-TEMPO (ppm) | EDA (ppm) | Total (ppm) | Induction (min.) |
|---|---|---|---|---|
| 1 | 0.0 | 0.00 | 0.0 | 30 |
| 2 | 0.0 | 100 | 100 | 30 |
| 3 | 0.0 | 400 | 400 | 30 |
| 4 | 4 | 50 | 54 | 177 |
| 5 | 4 | 100 | 104 | 200 |
| 6 | 4 | 400 | 404 | 307 |

TABLE III-continued

| No. | OH-TEMPO (ppm) | EDA (ppm) | Total (ppm) | Induction (min.) |
|---|---|---|---|---|
| 7 | 4 | 0.0 | 4 | 125 |

Data for the combination of OH-TEMPO and NH$_4$OH are presented in Table IV.

TABLE IV

| No. | OH-TEMPO (ppm) | NH$_4$OH (ppm) | Total (ppm) | Induction (min.) |
|---|---|---|---|---|
| 1 | 0.0 | 0.00 | 0.0 | 30 |
| 2 | 0.0 | 4 | 4 | 30 |
| 3 | 4 | 50 | 54 | 169 |
| 4 | 4 | 0.0 | 4 | 125 |

Chemicals that are neither synergistic nor antagonistic will react independent of each other. Chemicals that are synergistic when mixed will perform better than what is predicted by a linear combination of individual components. This synergism will be apparent by a curvature in the line upon plotting concentration of components versus performance. We see this effect clearly with the synergistic combination of DETA with the OH-TEMPO (FIG. 1).

The results of these tests demonstrate the enhanced activity or synergy between aliphatic amines and nitroxyl radical compounds at inhibiting vinyl monomer polymerization. These results also demonstrate that the combination of aliphatic amines with nitroxyl radical compounds is synergistic and unexpectedly more effective than would have been predicted by the linear combination of the individual components at inhibiting polymerization.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of vinyl monomers comprising adding to said vinyl monomers an effective inhibiting amount of a composition comprising (A) an aliphatic amine and (B) a nitroxyl radical compound.

2. The method as claimed in claim 1 wherein said aliphatic amine is selected from ethylenediamine, diethylenetriamine, butane-1,4-diamine, ethylamine, propylamine, butylamine, pentylamine, hexylamine, and cyclohexylamines 3. The method of claim 1 wherein said nitroxyl radical compound is selected from derivatives of dialkyl nitroxyl radicals, 1-oxyl-2,2,6,6-tetraalkylpiperidine compounds such as 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl)adipamide, N-1-oxyl-2,2,6,6-tetramethylpiperidin-4-yl-dodecylsuccinimide, 1-oxyl-4-methoxy-2,2,6,6-tetramethylpiperidine, 1-oxyl-4-amino-2,2,6,6-tetramethylpiperidine and 1-oxyl-4-acetamino-2,2,6,6-tetramethylpiperidine.

4. The method as claimed in claim 1 wherein said processing conditions are at temperatures of about 50° to about 150° C.

5. The method as claimed in claim 1 wherein said vinyl monomers are selected from the group consisting of olefins and diolefins.

6. The method as claimed in claim 5 wherein said olefins and said diolefins contain about 2 to about 20 carbons.

7. The method as claimed in claim 1 wherein said composition is added to said hydrocarbon in an amount ranging from about 1 to about 10,000 parts per million parts of said hydrocarbon.

8. The method of claim 1 wherein said monomer is undergoing processing.

9. The method of claim 1 wherein said nitroxyl radical compound is 1-xyl-2,2,6,6-tetramethylpiperidino-4-ol and said aliphatic amine is selected from ethylenediamine and diethylenetriamine.

10. A composition comprising (A) an aliphatic amine and (B) a nitroxyl radical compound.

11. The composition as claimed in claim 10 further comprising a vinyl monomer.

12. The composition as claimed in claim 10 wherein the weight ratio of (A) to (B) ranges from about 1:9 to about 9:1.

13. The composition of claim 10 wherein said nitroxyl radical compound is selected from derivatives of dialkyl nitroxyl radicals, 1-oxyl-2,2,6,6-tetraalkylpiperidine compounds such as 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl)adipamide, N-1-oxyl-2,2,6,6-tetramethylpiperidin-4-yl-dodecylsuccinimide, 1-oxyl-4-methoxy-2,2,6,6-tetramethylpiperidine and 1-oxyl-4-acetamino-2,2,6,6-tetramethylpiperidine.

14. The composition of claim 10 wherein the aliphatic amine is selected from ethylenediamine, diethylenetriamine, butane-1,4-diamine, ethylamine, propylamine, butylamine, pentylamine, hexylamine, and cyclohexylamines.

15. The composition of claim 13 wherein the nitroxyl compound is 1-oxyl-2,2,6,6-tetramethylpiperidino-4-ol.

16. The composition of claim 13 wherein the aliphatic amine is diethylenetriamine.

17. The composition of claim 13 wherein the aliphatic amine is ethylenediamine.

18. The composition of claim 10 wherein (A) is diethylenetriamine and (B) is 1-oxyl-2,2,6,6-tetramethylpiperidino-4-ol.

19. The composition of claim 18 wherein the weight ratio of (A) to (B) is about 1:9 to about 9:1.

* * * * *